(12) United States Patent
Geertsen (10) Patent No.: US 9,999,347 B2
(45) Date of Patent: Jun. 19, 2018

(54) HEADGEAR FOR OBSERVATION OF EYE MOVEMENTS

(71) Applicant: GN Otometrics A/S, Taastrup (DK)

(72) Inventor: Thomas Geertsen, Slagelse (DK)

(73) Assignee: Natus Medical Incorporated, San Carlos, CA (US)

( * ) Notice: Subject to any disclaimer, the term of this patent is extended or adjusted under 35 U.S.C. 154(b) by 0 days. days.

(21) Appl. No.: 14/642,715

(22) Filed: Mar. 9, 2015

(65) Prior Publication Data

US 2016/0256050 A1     Sep. 8, 2016

(30) Foreign Application Priority Data

Mar. 3, 2015   (DK) ........................... PA 2015 70118
Mar. 3, 2015   (EP) ..................................... 15157441

(51) Int. Cl.
| A61B 3/113 | (2006.01) |
| A61F 9/04 | (2006.01) |
| A61B 3/14 | (2006.01) |
| A61F 9/02 | (2006.01) |

(52) U.S. Cl.
CPC .............. *A61B 3/113* (2013.01); *A61B 3/145* (2013.01); *A61F 9/022* (2013.01); *A61F 9/04* (2013.01)

(58) Field of Classification Search
CPC ........... A61B 3/113; A61B 3/145; A61B 3/14; G06F 3/013; A61F 2009/00846; A61F 9/022; A61F 9/04
USPC ....................................................... 351/210
See application file for complete search history.

(56) References Cited

U.S. PATENT DOCUMENTS

| 1,642,661 A | 9/1927 | Robinson | |
| 4,331,136 A | 5/1982 | Russell et al. | |
| 4,815,839 A | 3/1989 | Waldorf | |
| 5,070,883 A * | 12/1991 | Kasahara | F41G 3/225 351/209 |
| 7,575,320 B1 * | 8/2009 | Kurup | G02C 11/02 351/203 |
| 8,708,141 B1 * | 4/2014 | Invie | A61F 9/04 206/223 |

(Continued)

FOREIGN PATENT DOCUMENTS

| JP | 2006 235139 A | 9/2006 |
| WO | WO 97/17020 A1 | 5/1997 |

(Continued)

OTHER PUBLICATIONS

First Technical Examination and Search Report dated Apr. 29, 2015, for corresponding Danish Patent Application No. PA 2015 70118, 5 pages.

(Continued)

*Primary Examiner* — Bumsuk Won
*Assistant Examiner* — Henry Duong
(74) *Attorney, Agent, or Firm* — Temmerman Law Office; Mathew J. Temmerman (57) ABSTRACT

An apparatus for covering eyes of a human includes: an eye piece configured for covering one of the eyes of the human; and an eye patch configured for covering the other one of the eyes of the human; wherein the eye piece and the eye patch are configured for preventing transmission of visible light; and wherein the eye piece comprises a region that is transparent for electromagnetic radiation with a wavelength range outside a visible range.

15 Claims, 8 Drawing Sheets

(56) References Cited

U.S. PATENT DOCUMENTS

| | | | |
|---|---|---|---|
| 2005/0193479 A1 | 9/2005 | Atta et al. | |
| 2010/0175174 A1* | 7/2010 | Chou ................... | A63B 33/002 2/446 |
| 2011/0034849 A1 | 2/2011 | Cooks | |
| 2011/0178585 A1* | 7/2011 | Biser ........................ | A61F 7/02 607/109 |
| 2015/0085257 A1* | 3/2015 | Masket ................ | A61F 13/124 351/222 |

FOREIGN PATENT DOCUMENTS

| | | | | |
|---|---|---|---|---|
| WO | WO 9717020 A1 * | 5/1997 | ............ | A61B 3/113 |
| WO | WO 2007/128034 A1 | 11/2007 | | |

OTHER PUBLICATIONS

Extended European Search Report dated Aug. 27, 2015 for corresponding European Patent Application No. 15157441.5, 7 pages.
International Search Report and Written Opinion dated May 12, 2016, for corresponding PCT Patent Application No. PCT/EP2016/054530, 13 pages.

\* cited by examiner

HEADGEAR FOR OBSERVATION OF EYE MOVEMENTS

RELATED APPLICATION DATA

This application claims priority to and the benefit of Danish Patent Application No. PA 2015 70118 filed Mar. 3, 2015, pending, and European Patent Application No. 15157441.5 filed Mar. 3, 2015, pending. The entire disclosures of both of the above applications are

FIELD OF TECHNOLOGY

A new apparatus is provided, with an eye piece and an eye patch, each of which is configured to cover a respective one of a human's eyes and thereby prevent visible light from reaching the human's eyes. The eye piece is transparent for electromagnetic radiation of wavelengths outside the visible range, e.g. infrared light, and/or ultraviolet light, etc.

The new apparatus may be disposable.

BACKGROUND

It is well-known to apply video technology to record and quantify eye movements. Typically, when eye movements are recorded, the human wears video goggles with a small infrared camera whereby one eye of the human, typically the right eye, is located within the viewing field of the camera, e.g. using a mirror to deflect infrared light from the eye into the camera.

Video goggles with two infrared cameras for recording eye movements of both eyes are also known.

For some measurements, prior art video goggles seek to prevent visible light from reaching the human's eyes in order to avoid suppression of reflex eye movements, for example nystagmus, due to optic fixation of the human's eyes. Thus, prior art video goggles desirably provide a complete light proof seal around its circumference when worn by the human so that no visible light is allowed to pass through the seal. The eyes of a human are extremely light sensitive, especially after having accommodated to darkness for a while so that light, even at very low intensities, illuminating the interior of the video goggles may undesirably suppress reflex eye movements.

The required light proof seal is difficult to obtain with prior art video goggles that are intended to be used by different humans with different facial anatomy and often, doctors prefer to study eye movements in a dark room despite the fact that this makes the study much more cumbersome to perform.

The prior art video goggles also require proper cleaning between use by different humans.

SUMMARY

In order to overcome the above-mentioned and other difficulties, an apparatus with one eye piece and one eye patch is provided that isolates the human's eyes visually from the surroundings so that the human experiences complete darkness, or substantially complete darkness. The eye piece and the eye patch are made opaque to visible light, and each of the eye piece and the eye patch is configured to form a lightproof seal around the respective eye when worn by the human.

When the eye piece and the eye patch is worn by the human in their intended operational positions covering the respective eyes of the human, the human should experience substantially complete darkness, i.e. the human experiences absence of illumination so that the human has nothing to direct his or her line of sight towards within his or her field of view.

Throughout the present disclosure, a posterior surface is a surface that is intended to face towards a skin surface of a human during normal use, and an anterior surface is a surface that is intended to face away from a skin surface of a human towards surroundings of the human during normal use.

Thus, an apparatus is provided that is configured for covering the eyes of a human and comprises an eye piece configured for covering one of the eyes, e.g. the right eye, of the human, and an eye patch configured for covering the other one of the eyes, e.g. the left eye, of the human, and wherein the eye piece and the eye patch are configured for preventing transmission of visible light, and wherein the eye piece comprises a region that is transparent for electromagnetic radiation with a wavelength range outside a visible range.

A device is also provided to be worn above a shoulder of a human, comprising a structure, at least one camera coupled to the structure, and the apparatus, wherein the camera is coupled to the structure so that the region of the eye piece of the apparatus is positioned in the field of view of the camera during use.

When eye movements need only be recorded of one eye, the other eye is covered with an opaque eye patch that forms a light proof seal separating the eye from the surroundings and preventing visible light from reaching the eye in a simple, flexible, effective and inexpensive way.

The eye patch is made of a material that is opaque to visible light. The material may be a flexible plastic material that is easily shaped to conform to the facial anatomy of the eye and its surroundings.

For example, polyamide and polyester are suitable materials with desired characteristics, such as high durability, capability of transporting and absorbing moisture, breathability, and opaque.

The eye patch may comprise an antimicrobial agent, for example an antibacterial agent. The patch may be coated or impregnated with the antimicrobial agent.

The eye patch can be mounted at the respective eye of the human individually and independent of the mounting of eye piece in order to prevent visible light from reaching the respective eye. The individual and independent positioning of the eye patch makes it easy to establish a lightproof seal around the human's eyes with standard sized and standard shaped eye patches, i.e. eye patches that are not customized to individually fit the facial anatomy of a specific human.

Preferably, the eye patch is retained against the human's skin using an adhesive applied to the eye patch, e.g. the eye patch may have an adhesive surface intended for attachment to a skin surface.

The adhesive surface preferably includes a layer of a flexible material, such as polyethylene foam, silicone, molded TPE, etc., to provide a sealing surface that better accommodates uneven facial surfaces.

The adhesive surface may reside on the flexible material.

The adhesive may be a gentle acrylic adhesive for skin adhesion.

The adhesive may be an adhesive polymer layer or hot melt adhesive or polyurethane and/or combination of hydroselective adhesive. For example, the adhesive may comprise silicone resin. Silicone resin has been found to minimise skin trauma and allergies.

The eye patch may have a non-adhesive flap preferably located at the temporal end of the eye patch and intended for gripping between two fingers for easy removal of the eye patch after use.

The adhesive surface may comprise a layer of an adhesive tape secured to the eye patch, such as 2477P which is a double coated synthetic rubber/gentle acrylic adhesive tape designed for medical applications supplied by 3M Medical Specialties.

The flexible material may be included in the adhesive tape.

The adhesive may be part of a double-sided adhesive tape, the double-sided tape having an additional adhesive surface adhering to a posterior surface of the eye patch.

The tape may have a non-adhesive flap residing at the temporal end of the tape intended for gripping between two fingers for easy removal of the tape; or, the eye patch together with the tape, after use.

Preferably, the double-sided tape is discarded after use so that the requirement of cleaning eye patches between uses is reduced.

The eye patch may have a peripheral edge that comprises the adhesive.

The inner part of the eye patch inside the peripheral edge may not have an adhesive for easy removal of the eye patch after use.

Attachment to a facial skin surface with an adhesive facilitates formation of a lightproof seal between the eye patch and the skin surface. The lightproof seal does not transmit visible light. Since skin is flexible, skin adhering to the eye patch is capable of staying attached to the adhesive surface even if the adhering surface moves slightly. Thus, pressing an adherent and flexible surface of an eye patch against a facial surface around an eye of a human ensures formation of the lightproof seal. The lightproof seal is maintained when the pressure is relieved even if the adhesive surface does not conform exactly to the relaxed anatomy of the skin surface to which it is attached, since the skin is capable of deforming into the shape of the adhesive surface that approximately conforms to the facial surface around the eye in question.

The peripheral edge of the eye patch may be shaped to conform to an area surrounding the respective eye, e.g., an area within and proximate, possibly including, an orbital rim of the respective eye.

The peripheral edge may be sized and shaped such that at least parts of the upper and lower nasal portions of the peripheral edge are positioned within the adjacent margins of the orbital rim, or within the outer margins of the orbicularis oculi muscles. The adhesive surface of the upper and lower nasal portions generally seats against soft tissue within the orbital rim, or against the fibers of the orbicularis oculi muscles, and the adhesive surface at the upper and lower temporal portions of the peripheral edge generally seats against the adjacent temporal margins of the orbital rims.

The eye patch may be sized and shaped to fit substantially or entirely within the orbital rims; or, the eye patch may be sized and shaped to cover the orbital rim.

The eye patch may have a protruding section, which is intended to cover the eye with a distance to the closed eye lid, and a peripheral edge extending around the protruding section, or at least a portion of the protruding section, and optionally comprising an adhesive that secures the eye patch to the skin surface.

The protruding section of the eye patch allows the human to move his or her eye and/or blink the eye covered by the eye patch without obstruction and discomfort.

The eye patch may have a head strap that is configured for fitting around the head of the human for securing the eye patch in its intended position during use covering the respective eye of the human preventing visible light from reaching the respective eye of the human.

The eye patch with the head strap may not have an adhesive surface.

Preferably, the human closes his or her eye lid before and during application of the eye patch to the eye in question.

In order to be able to record eye movements, e.g. with an infrared camera, the eye piece has a region, e.g. a window, that is transparent for electromagnetic radiation with wavelengths outside the visible range, i.e. electromagnetic radiation with wavelengths residing outside a visible range from 400 nm-700 nm, such as infrared light, e.g., infrared light ranging from 700 nm-1 mm, such as infrared light ranging from 700 nm-5200 nm, preferably from 740 nm-2000 nm, more preferred from 852 nm to 1100 nm, ultraviolet light, e.g. ultraviolet light ranging from 20 nm-400 nm, such as ultraviolet light ranging from 200 nm-400 nm, preferably from 300 nm to 400 nm, more preferred from 320 nm to 380 nm.

The structure may comprise video goggles and the apparatus with the eye piece and the eye patch may be worn by the human underneath the video goggles, i.e. between the eyes and the video goggles. The video goggles have camera(s) attached thereto that is/are capable of recording electromagnetic radiation outside the visible range passing through the region, e.g. infrared camera(s), ultraviolet camera(s), etc, for observation of eye movements, such as nystagmus. The video goggles also comprise sources of electromagnetic radiation for illumination of the eye(s) with the electromagnetic radiation outside the visible range, for example infrared light diodes, ultraviolet diodes, etc.

Since darkness is provided by the apparatus with the eye piece and the eye patch, the separate video goggles need not be opaque to visible light and in particular do not need to provide a lightproof seal around the eyes of the human, making it much easy to fit the video goggles to humans with different facial anatomy. This also reduces the effort of cleaning the video goggles between uses.

The video goggles may have the form of a helmet or a mask.

Since the eye piece and the eye patch prevent visible light from reaching the human's eyes and thereby suppress optic fixation of the human's eyes, the camera needs not be arranged in goggles, i.e. the structure may not include video goggles, but the camera may be arranged in another way so that the eye for which eye movements, such as nystagmus, are to be observed resides in the field of view of the camera.

The region may have any of various configurations. For example, the region may have a flat anterior surface. In another example, the region has two flat surfaces forming an angle; or, in yet another example, the region has a curved, convex anterior surface, e.g. for moving a possible reflection of a source of electromagnetic radiation, such as IR LEDs, out of the field of view of a camera used for eye movement recording.

In addition, the region may have various tints or coatings (e.g., an anti-reflection coating), for improved image formation as known in the art.

The region may be made of a material transparent for infrared light, such as an acrylic material, such as the infrared transparent material PC Makrolon 2405, colour: 452601.

Alternatively, the region may be made of a material that is transparent for visible light; however coated with a material that is opaque to visible light. The coating may be the so-called Cold Mirror CM-05 material, see http://www.optical-filters.com/Cold_Mirror_CM-05_Transmission_Data.aspx, The region may have a transmittance, i.e. the fraction of incident electromagnetic radiation at a specified wavelength that passes through the region, of more than 52%, preferably more than 60%, more preferred more than 70%, most preferred more than 80% of infrared light in the wavelength range from 852-1100 nm.

Each of the eye piece and the eye patch may have a transmittance of less than 1% of visible light in the wavelength range from 380 nm-740 nm.

The eye piece is made of a material that is opaque to visible light. The material may be a plastic material, such as a soft plastic material, or a hard plastic material, such as a standard hard black plastic.

The eye piece may comprise a frame with an aperture for accommodation of the region, e.g. a window, and made of another material than the material of the region, such as a plastic material, such as a soft plastic material, or a hard plastic material, such as a standard hard black plastic.

Alternatively, the eye piece may be made of the material of the region so that the frame and region constitute a single part.

The eye piece may comprise a peripheral flange that is shaped to conform to an area surrounding the respective eye, e.g., an area within and proximate, possibly including, an orbital rim of the respective eye.

The eye piece can be mounted at the respective eye of the human individually and independent of the mounting of the eye patch, for prevention of visible light from reaching the respective eye. The individual and independent positioning of the eye piece and the eye patch makes it easy to establish a lightproof seal around the human's eyes with standard sized and standard shaped eye pieces and eye patches, i.e. eye pieces and eye patches that are not customized to individually fit the facial anatomy of a specific human.

The eye piece may be retained against the human's face using an adhesive applied to the eye piece, e.g. the eye piece may have an adhesive surface intended for attachment to a skin surface.

The peripheral flange of the eye piece may have a non-adhesive flap preferably located at the temporal end of the flange and intended for gripping between two fingers for easy removal of the eye piece after use.

Preferably, both the eye piece and the eye patch are retained against the human's face using an adhesive applied to the eye piece and the eye patch, respectively, e.g. both the eye piece and the eye patch may have adhesive surfaces intended for attachment to a skin surface.

The surface intended for attachment to a skin surface preferably includes a layer of a flexible material, such as polyethylene foam, silicone, molded TPE, etc, to provide a sealing surface that better accommodates uneven facial surfaces.

The adhesive surface may reside on the flexible material.

The adhesive may be a gentle acrylic adhesive for skin adhesion.

The adhesive surface may comprise a layer of an adhesive tape, such as 2477P which is a double coated synthetic rubber/gentle acrylic adhesive tape designed for medical applications supplied by 3M Medical Specialties, that is secured to the eye piece and/or the eye patch.

The flexible material may be included in the adhesive tape.

The adhesive may be part of a double-sided adhesive tape, the double-sided tape having an additional adhesive surface adhering to a posterior surface of the eye piece.

Preferably, the double-sided tape is discarded after use so that the requirement of cleaning eye pieces between uses is reduced.

The tape may have a non-adhesive flap residing at the temporal end of the tape intended for gripping between two fingers for easy removal of the tape; or, the eye piece together with the tape, after use.

Attachment to a facial skin surface with an adhesive facilitates formation of a lightproof seal between the eye piece and the skin surface. Since skin is flexible, skin adhering to the eye piece is capable of staying attached to the adhesive surface even if the adhering surface moves slightly. Thus, pressing an adherent and flexible surface of an eye piece against a facial surface around an eye of a human ensures formation of a lightproof seal. The lightproof seal prevents transmission of visible light from the surroundings to the eye covered by the eye piece. The lightproof seal is maintained when the pressure is relieved even if the adhesive surface does not conform exactly to the relaxed anatomy of the skin surface to which it is attached, since the skin is capable of deforming into the shape of the adhesive surface that approximately conforms to the facial surface around the eye in question.

The eye piece may comprise a transversal portion that is positioned in front of one of the eyes when worn by the human, and an annular peripheral wall that extends around the transversal portion and rearward there from, and a peripheral flange connected to the peripheral wall and shaped to conform to the shape of the eye surroundings.

At the inner peripheral edge of the flange, where the flange is joined to the wall, but on the opposite side of the flange, the eye piece may further have a peripheral barrier wall extending inwardly on the other side of the flange in the direction of the eye during use for further prevention of visible light reaching the eye. The barrier wall preferably does not abut tissue of the human during use. Preferably, the height of the barrier wall is increased proximate the nasal end of the flange residing proximate the side wall of the nose during use due to the typically irregularly shaped surfaces in this area of the eye surroundings. Irregularly shaped surfaces may be more difficult to conform to with the eye piece thereby making it more difficult to obtain a light proof seal with abutting surfaces alone in this area than elsewhere.

A method of determining an eye movement is also provided, comprising the steps of:
providing an apparatus having
a. an eye piece and an eye patch, and
b. a camera, wherein
c. the eye piece and the eye patch are opaque to visible light, and
d. the eye piece comprises a region that is transparent for electromagnetic radiation with a wavelength range outside a visible range;
covering the eyes of a human with the eye piece and the eye patch, respectively, thereby preventing visible light from reaching the eyes of the human, and
tracking movements of the eye covered with the eye piece using the camera.

A method of determining eye movement is also provided, comprising the steps of
mounting the apparatus with the eye piece and the eye patch on the head of a human for preventing visible light from reaching the eyes of the human,
mounting one camera so that the eye covered with the eye piece is situated within the field of view of the camera, and
tracking eye movements with the camera.

The methods may further comprise discarding at least part of the apparatus with the eye piece and the eye patch after tracking.

Preferably, the eye piece and the eye patch are discarded after use with the same human, whereby the requirement of cleaning the eye piece and eye patch between uses with different humans is eliminated.

An apparatus for covering eyes of a human includes: an eye piece configured for covering one of the eyes of the human; and an eye patch configured for covering the other one of the eyes of the human; wherein the eye piece and the eye patch are configured for preventing transmission of visible light (e.g., some visible light, substantially all visible light, or all visible light); and wherein the eye piece comprises a region that is transparent for electromagnetic radiation with a wavelength range outside a visible range. As used in this specification, the term "substantially all visible light" refers to at least 75% of all visible light, and more preferably at least 90% of all visible light, and even more preferably at least 99% of all visible light. The percentage may be determined using different metrics (e.g., intensity, frequency range, etc.) in different embodiments.

Optionally, the eye patch has a head strap that is configured for fitting around a rear of a head of the human for securing the eye patch relative to the head of the human.

Optionally, the eye patch comprises an adhesive surface for adhesively securing the eye patch to a skin surface of the human.

Optionally, the adhesive surface comprises a layer of adhesive tape that is secured to the eye patch.

Optionally, the adhesive surface is a part of a double-sided tape, the double-sided tape having an additional adhesive surface adhering to a posterior surface of the eye patch.

Optionally, the eye piece comprises an adhesive surface for adhesively securing the eye piece to a skin surface of the human.

Optionally, the adhesive surface is on a flexible material.

Optionally, the adhesive surface comprises a layer of adhesive tape that is secured to the eye piece.

Optionally, the adhesive surface is a part of a double-sided tape, the double-sided tape having an additional adhesive surface adhering to a posterior surface of the eye piece.

Optionally, the region comprises a first material that is transparent for visible light, and a second material that is opaque to visible light, the second material coating the first material.

Optionally, the eye piece comprises a frame with an aperture for accommodation of a window that defines the region, the frame being made of a material that is different from a material of the window.

Optionally, the eye piece comprises a peripheral flange having a shape that corresponds with a shape of an orbital rim.

Optionally, the eye piece comprises (1) a transversal portion that is positioned in front of one of the eyes when the apparatus is used by the human, (2) an annular peripheral wall that surrounds the transversal portion and extends rearward therefrom, and (3) a peripheral flange surrounding the peripheral wall and having a shape that corresponds with a shape of an orbital rim of the one of the eyes.

A device for worn above a shoulder of a user includes: a structure; at least one camera coupled to the structure; and the apparatus according to any of the embodiments described herein; wherein the at least one camera is coupled to the structure so that the region of the eye piece of the apparatus is positioned in a field of view of the at least one camera.

A method of determining an eye movement includes: providing an apparatus having an eye piece and an eye patch, and a camera, wherein the eye piece comprises a region that is transparent for electromagnetic radiation with a wavelength range outside a visible range; preventing visible light from reaching eyes of a human using the eye piece and the eye patch; and tracking a movement of the eye that is covered by the eye piece using the camera.

Other features, advantageous, and embodiments will be described in the detailed description.

BRIEF DESCRIPTION OF THE DRAWINGS

The drawings illustrate the design and utility of embodiments, in which similar elements are referred to by common reference numerals. These drawings may or may not be drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

In the drawings.

DETAILED DESCRIPTION

Various illustrative examples of the new eye piece, new eye patch, headgear and method according to the appended claims will now be described more fully hereinafter with reference to the accompanying drawings, in which various embodiments of the new eye piece and new eye patch, headgear and method are illustrated. The new eye piece and new eye patch; headgear and method according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described. It should also be noted that the accompanying drawings are schematic and simplified for clarity, and they show sufficient details for the understanding of the new eye piece and new eye patch, headgear and method.

As used herein, the singular forms "a," "an," and "the" refer to one or more than one, unless the context clearly dictates otherwise.

FIGS. 1-7 illustrate one exemplary new apparatus 10 with the eye piece 12 and the eye patch 14, each of which is configured to isolate a respective one of a human's eyes from visible light of the surrounding environment.

Figure 1:
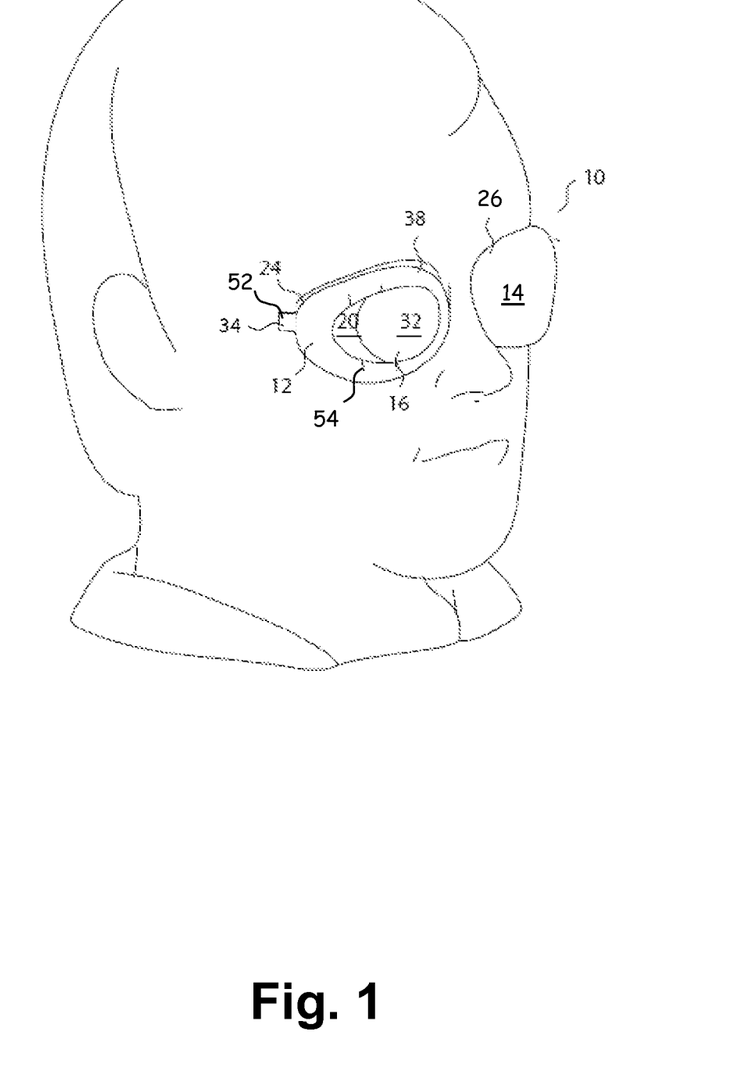
FIG. 1 schematically shows a perspective view of a human's head with an example of the new eye piece and new eye patch, FIG. 2 schematically shows the human's head from the side with the new eye piece also shown in FIG. 1, FIG. 3 schematically shows an exploded perspective view of the new eye piece and new eye patch of FIG. 1 behind video goggles with an IR camera, FIG. 4 schematically shows a perspective view of the new eye piece and new eye patch of FIG. 1 behind video goggles with an IR camera, FIG. 5 schematically shows an exploded perspective view of the new eye piece and new eye patch of FIG. 1.

FIG. 1 shows in perspective the apparatus 10 mounted in its intended operating position covering the eyes of a human so that the human is unable to see anything. In the illustrated example, the eye piece 12 covers the right eye of the human and comprises a transversal portion 16 spanning substantially perpendicular to a forward looking direction of the human, when the apparatus 10 with the eye piece 12 and the eye patch 14 is mounted in its intended operational position on the human's head. The eye piece 12 further has a curved annular peripheral wall 20 surrounding and supporting the transversal portion 16. The wall 20 has a flange 24 with a posterior surface 28 that is configured to be attached to the skin surface of the human at, or adjacent, the orbital rims.

Figure 5:
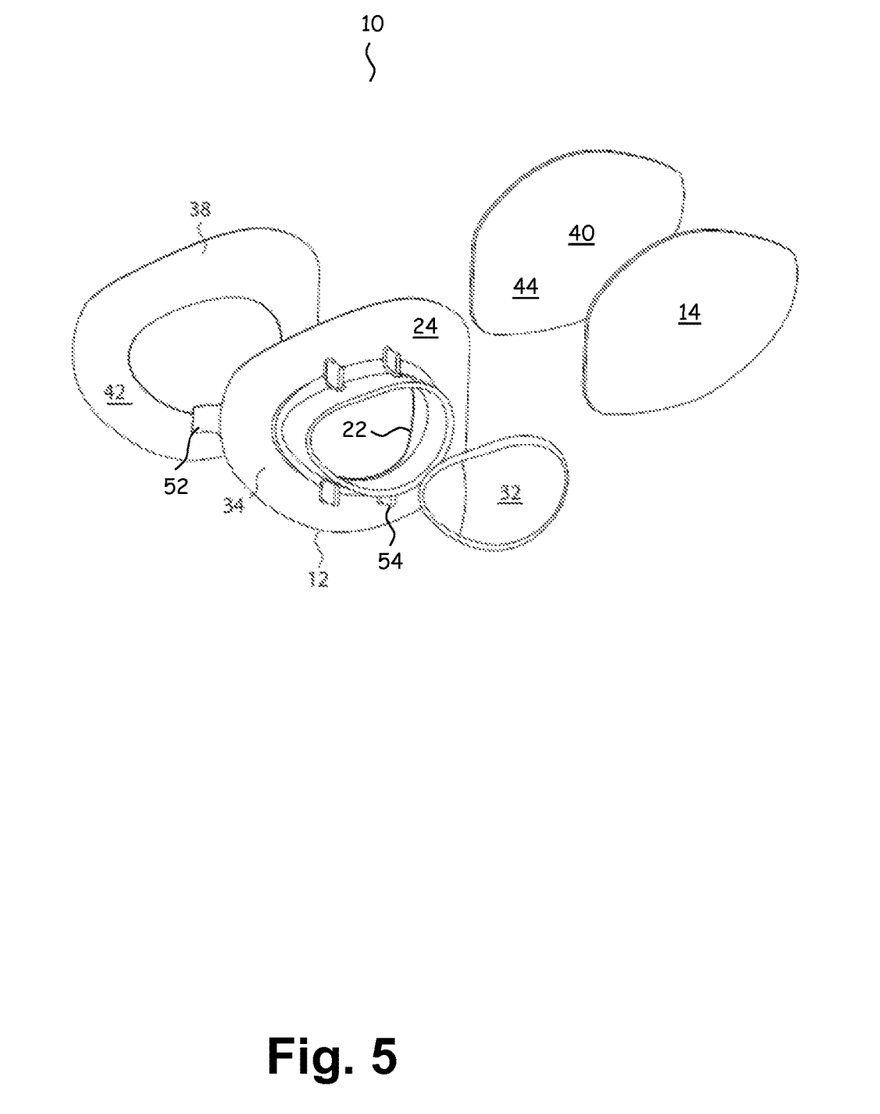
Figure 6:
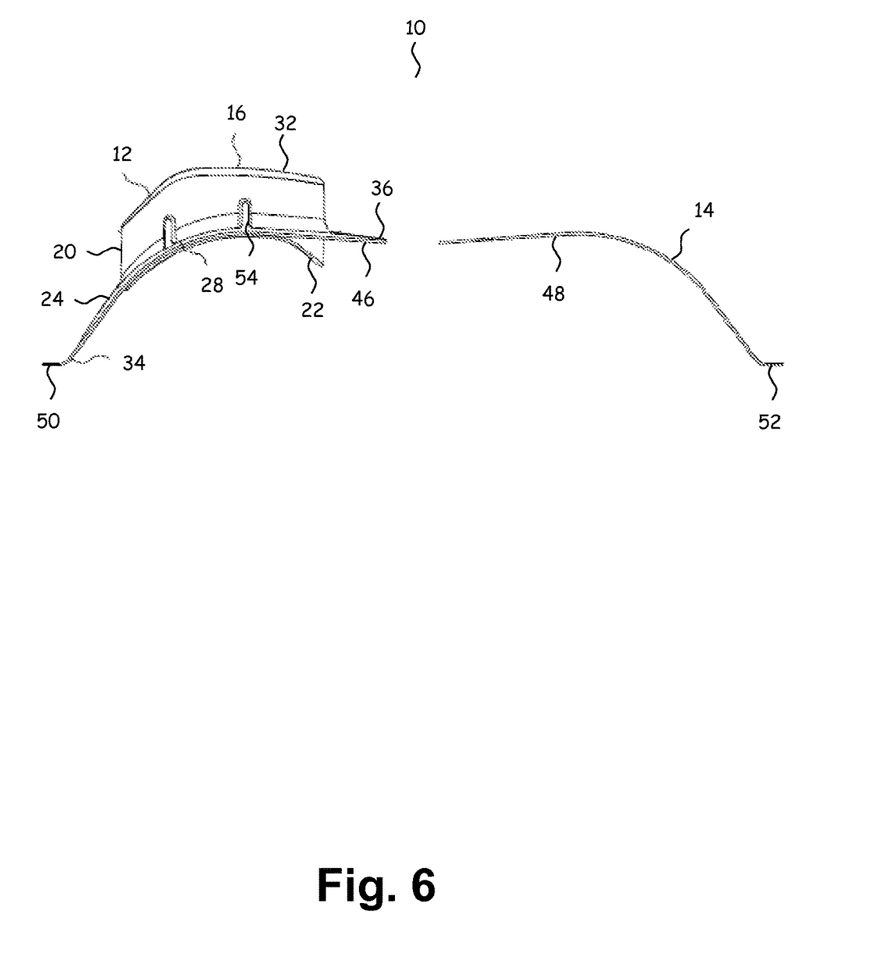
FIG. 6 is a bottom view of the new eye piece and new eye patch shown in FIG. 1.

At the inner peripheral edge of the flange 24, where the flange 24 is joined to the wall 20, but on the opposite side of the flange 24, the eye piece 12 has a peripheral barrier wall 22, FIGS. 5 and 6, extending inwardly on the other side of the flange 24 in the direction of the eye during use for further prevention of visible light reaching the eye. The barrier wall 22 preferably does not abut tissue of the human during use. The height of the barrier wall 22 is increased proximate the nasal end 36 of the flange 24 residing proximate the side wall of the nose during use due to the typically irregularly shaped surfaces in this area of the eye surroundings. The surface of the eye piece 12 may not fit the Irregularly shaped surfaces sufficiently accurately to form the required light proof seal and therefore the barrier wall 22 has been added in order to make sure that also in this area of the eye surroundings, a light proof seal is formed with the eye piece 12.

The eye piece 12 has a region 32 in its transversal portion 16 that is transparent for infrared light so that observation of the right eye of the human can be performed with an infrared camera. When the eye piece 12 and the eye patch 14 are mounted in their intended operational positions covering the right eye and left eye, respectively, they form a substantially light proof seal with the face of a human and thereby prevent visible light from reaching the human's eyes, whereby suppression of involuntary eye movements, such as nystagmus, is avoided. This is due to the fact that the eyes are not presented with an illuminated feature that the line of sight of the eyes can be aligned with.

The eye piece 12 is preferably constructed from a relatively stiff and hard opaque plastic, with good scratch resistance and optical qualities. A suitable plastic is an impact-resistant polycarbonate material, although various other materials are also usable.

The region 32 is made of a material transparent for infrared light, such as an acrylic material, such as the infrared transparent material PC Makrolon 2405, colour: 452601.

The region 32 of the eye piece 12 can have any of various configurations. In the illustrated eye piece 12, the region 32 includes a flat anterior portion and, as most clearly illustrated in FIG. 6, a second flat portion forming an angle with the flat anterior portion so that possible reflections of infrared light emitted for illumination of the eye covered by the eye piece are moved out of the field of view of the infrared camera positioned for recording the eye movements. In addition, the region 32 can have various tints or coatings (e.g., an anti-reflection coating), for improved image quality as known in the art.

The flange 24 is sized and shaped such that upper and lower nasal portions of the flange are positioned within the adjacent margins of the orbital rim, or within the outer margins of the orbicularis oculi muscles. The posterior surface 28 (shown in FIG. 6) of the upper and lower nasal portions generally seats against soft tissue within the orbital rim, or against the fibers of the orbicularis oculi muscles, and posterior surface 28 of the upper and lower temporal portions of the flanges 24 generally seats against the adjacent temporal margins of the orbital rims.

It is not necessary that the entire eye piece fit within the orbital rim or be engageable by the orbicularis oculi muscles. It is possible, for example, that the muscles only engage and retain a portion (such as a nasal or temporal portion) of the eye piece.

In addition, the human can affect the exact positioning of the eye piece 12 with respect to the orbital rim. For example, by angling the transversal portion 16 slightly downwardly with respect to the normal line of sight, a human can position the eye piece such that the upper nasal portion the lower nasal portion and the lower temporal portion except for the temporal end 34 are positioned within the orbital rim. In addition, the positioning of the flange 24 relative to the orbital rim can vary slightly depending on the facial morphology of the human.

In an alternative embodiment, the flange 24 can be sized and shaped to fit substantially or entirely within the orbital rims. In another alternative embodiment, the flange 24 can be sized and shaped to reside completely outside the orbital rim.

Dimensions of the eye piece 12 may be determined using many different approaches. For example, the eye piece 12 and the eye patch 14 can be custom designed and fitted to a particular individual. Preferably, the dimensions can be determined by reference to a standard head form that has been designed according to statistical norms from the population, or from published texts and descriptions of such norms.

In the illustrated eye piece 12, the region 32 and the transversal portion 16 are separately formed from different materials and then subsequently joined together to form the eye piece 12.

The region 32 can be either permanently attached to the transversal portion 16 or connected to the transversal portion in a removable manner.

In another apparatus 10 with the eye piece 12 and the eye patch 14, the eye piece 12 has a one-piece or unitary construction.

To assist in retaining the eye piece 12 against the face of the human, the illustrated eye piece 12 has an adhesive surface provided by an adhesive tape 38, overlaying the respective posterior surface 28, see FIG. 6. The adhesive tape 38 can be conventional "double-sided" or "double-coated" tape having a first adhesive surface 42 secured to the posterior surface 28 of the eye piece 12, and a second adhesive surface 46 that is adhered to the skin of the human. The eye piece 12 can include a removable, protective cover layer (not shown) overlaying the second adhesive surface 46 of the tape to protect the second adhesive surface 46 from adhering to extraneous matter prior to use.

The eye piece 12 has a non-adhesive flap 52 located at the temporal end 34 of the eye piece 12 and intended for gripping between two fingers for easy removal of the eye piece 12 after use.

The eye piece 12 can be provided with a separate piece of double-sided adhesive tape 38 that is shaped to fit and be applied to the posterior surface 28 of the eye piece 12, and a set of instructions for informing a human how to apply the tape to the eye piece.

The second adhesive surface 46 desirably exhibits a bonding strength suitable for adherence of the eye piece 12 to the skin of the human during normal conditions of use, yet allows the eye piece 12 to be removed with minimal discomfort. The first adhesive surface 42 of the tape desirably provide a bonding strength sufficient to prevent separation of the tape from the eye piece 12 during normal conditions of use and during removal of the eye piece.

The tape 38 may have a non-adhesive flap (not shown) residing at the temporal end of the tape intended for gripping between two fingers for easy removal of the tape 38; or, the eye piece 12 together with the tape 38, after use.

In the illustrated example, the double sided tape is discarded before use of the eye piece 12 by another human, in that the first adhesive surface 42 also allows the tape to be peeled away from the posterior surface 28 of the eye piece 12 to permit replacement of the tape, when the eye piece 12 has been removed from the human after use, and subsequently will be used again by the same or another human.

The posterior surface 28 preferably includes a layer of a flexible material, such as polyethylene foam, to provide a sealing surface that better accommodates uneven facial surfaces. The flexible material may be included in the adhesive tape. The adhesive may form a layer of an adhesive tape 38, such as 2477P which is a double coated synthetic rubber/gentle acrylic adhesive tape designed for medical applications supplied by 3M Medical Specialties.

In another example, a layer of a suitable adhesive (e.g., acrylic) may be formed directly on the posterior surface 28 of the eye piece 12.

The illustrated eye piece 12 further has four ribs extending a short distance outwardly from the wall 20 towards the peripheral edge of the eye piece 12. The ribs 54 fit respective inner surfaces of the video goggles 100 so that the video goggles 100 are properly aligned with the eye piece 12, when the video goggles 100 are mounted in its intended operational position over the eye piece 12 and the eye patch 12, and so that the eye piece 12 is not unintentionally dislocated from its intended position with risk of breaking the light proof seal, when the video goggles 100 are mounted.

Instead of providing a second eye piece for covering the other eye that is similar to the illustrated eye piece 12, an opaque eye patch 14 is provided that covers the other eye and forms a light proof seal separating the other eye from the surroundings and prevents visible light from reaching the eye in a simple, flexible, effective and inexpensive way.

The eye patch 14 is made of a material that is opaque to visible light. The material is a flexible plastic material that is easily shaped to conform to the facial anatomy of the eye and its surroundings.

For example, polyamide and polyester are suitable materials with desired characteristics, such as high durability, capability of transporting and absorbing moisture, breathability, and opaque.

The eye patch 14 may comprise an antimicrobial agent, for example an antibacterial agent. The eye patch 14 may be coated or impregnated with the antimicrobial agent.

As opposed to mounting goggles with two interconnected eye pieces, the eye patch 14 is mounted at the respective eye of the human individually and independent of the mounting of the eye piece 12. The flexibility of the eye patch 14 and individual and independent mounting of the eye patch 14 makes it easy to establish a lightproof seal around the human's eye with a standard sized and standard shaped eye patch 14, i.e. an eye patch that is not customized to individually fit the facial anatomy of the human in question.

The illustrated eye patch 14 is retained against the human's skin using an adhesive applied to the eye patch 14, e.g. the eye patch 14 has an adhesive surface intended for attachment to a skin surface.

The adhesive surface preferably includes a layer of a flexible material, such as polyethylene foam, silicone, molded TPE, etc., to provide a sealing surface that accommodates uneven facial surfaces.

The adhesive surface may reside on the flexible material.

The adhesive may be a gentle acrylic adhesive for skin adhesion.

The adhesive may be an adhesive polymer layer or hot melt adhesive or polyurethane and/or combination of hydroselective adhesive. For example, the adhesive may comprise silicone resin. Silicone resin has been found to minimise skin trauma and allergies.

The adhesive surface may comprise a layer of an adhesive tape, such as 2477P which is a double coated synthetic rubber/gentle acrylic adhesive tape designed for medical applications supplied by 3M Medical Specialties and secured to the eye patch.

The flexible material may be included in the adhesive tape.

In the illustrated eye patch 14, the adhesive is part of a double-sided adhesive tape 40, the double-sided tape 40 having an additional adhesive surface adhering to a posterior surface 30 of the eye patch 14.

Preferably, the double-sided tape 40 is discarded after use so that the requirement of cleaning eye patches between uses is reduced.

The eye patch 14 may have a peripheral edge 26 that comprises the adhesive.

The inner area of the eye patch 14 surrounded by the adhesive peripheral edge 26 may not be adhesive whereby removal of the eye patch 14 after use is facilitated.

Attachment to a facial skin surface with an adhesive facilitates formation of a lightproof seal between the eye patch 14 and the skin surface. The lightproof seal does not transmit visible light. Since skin is flexible, skin adhering to the eye patch 14 is capable of staying attached to the adhesive surface even if the adhering surface moves slightly. Thus, pressing an adherent and flexible surface of an eye patch 14 against a facial surface around an eye of a human ensures formation of the lightproof seal. The lightproof seal is maintained when the pressure is relieved even if the adhesive surface does not conform exactly to the relaxed anatomy of the skin surface to which it is attached, since the skin is capable of deforming into the shape of the adhesive surface that approximately conforms to the facial surface around the eye in question.

The peripheral edge 26 of the illustrated eye patch 14 is shaped to conform to an area surrounding the respective eye, e.g., an area within and proximate, possibly including, an orbital rim of the respective eye.

The peripheral edge 26 is sized and shaped such that upper and lower nasal portions of the flange are positioned within the adjacent margins of the orbital rim, or within the outer margins of the orbicularis oculi muscles. The adhesive surface of the upper and lower nasal portions generally seats against soft tissue within the orbital rim, or against the fibers of the orbicularis oculi muscles, and the adhesive surface at the upper and lower temporal portions of the peripheral edge 26 generally seats against the adjacent temporal margins of the orbital rims.

The eye patch 14 can be sized and shaped to fit substantially or entirely within the orbital rims; or, the eye patch 14 can be sized and shaped to cover the orbital rim.

The eye patch 14 may have a protruding section (not shown), which is intended to cover the eye with a distance to the closed eye lid, and an adhesive peripheral edge 26 extending around the protruding section, or at least a portion of the protruding section, securing the eye patch 14 to the skin surface.

The protruding section of the eye patch 14 allows the human to move his or her eye and blink the eye that is covered by the eye patch 14 without obstruction and discomfort.

Preferably, the illustrated new apparatus 10 is discarded after removal from the human, whereby a need of proper cleaning of the eye piece between uses by different humans is eliminated.

The eye piece 12 and the eye patch 14 facilitates individual lightproof positioning of the parts across the respective eye, since each part can be freely oriented and applied to the face of the human independent of the orientation and positioning of the other part.

Figure 2:
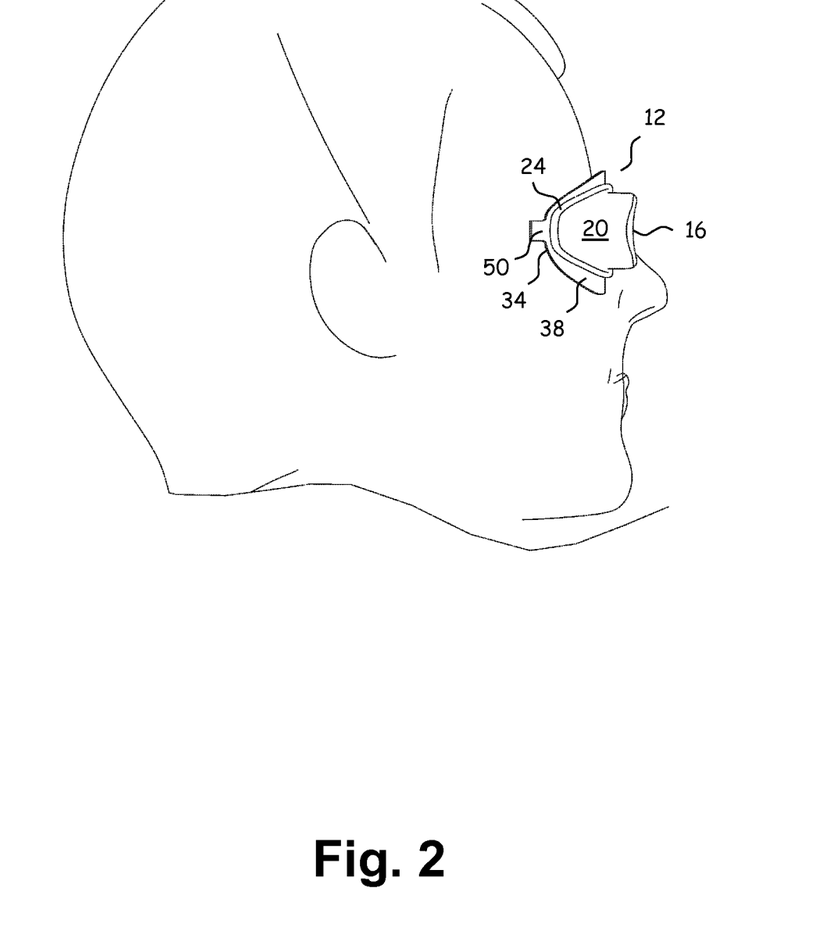

FIG. 2 shows from the right side of the human, the eye piece 12 of the apparatus 10 shown in FIG. 1, mounted in its intended operating position covering the right eye of the human so that the human is unable to see anything with the right eye.

Figure 3:
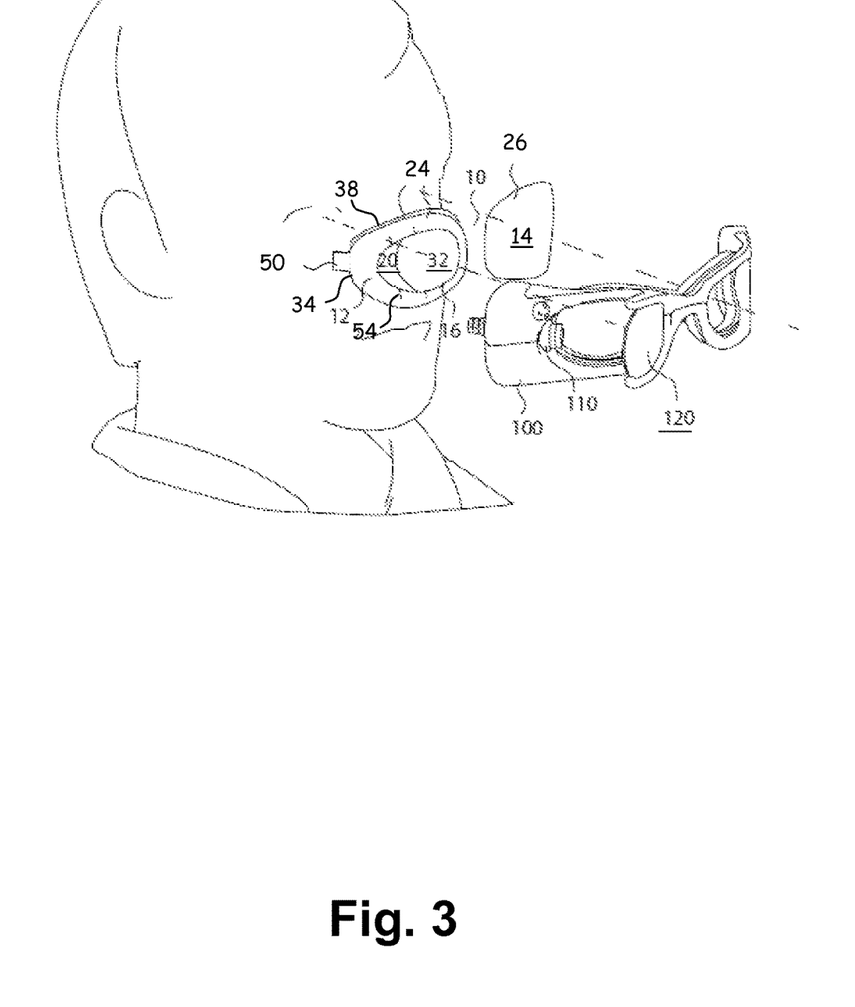

FIG. 3 is a schematic exploded view of an assembly of the new apparatus 10 shown in FIG. 1 and video goggles 100. The video goggles 100 form the structure.

Figure 4:
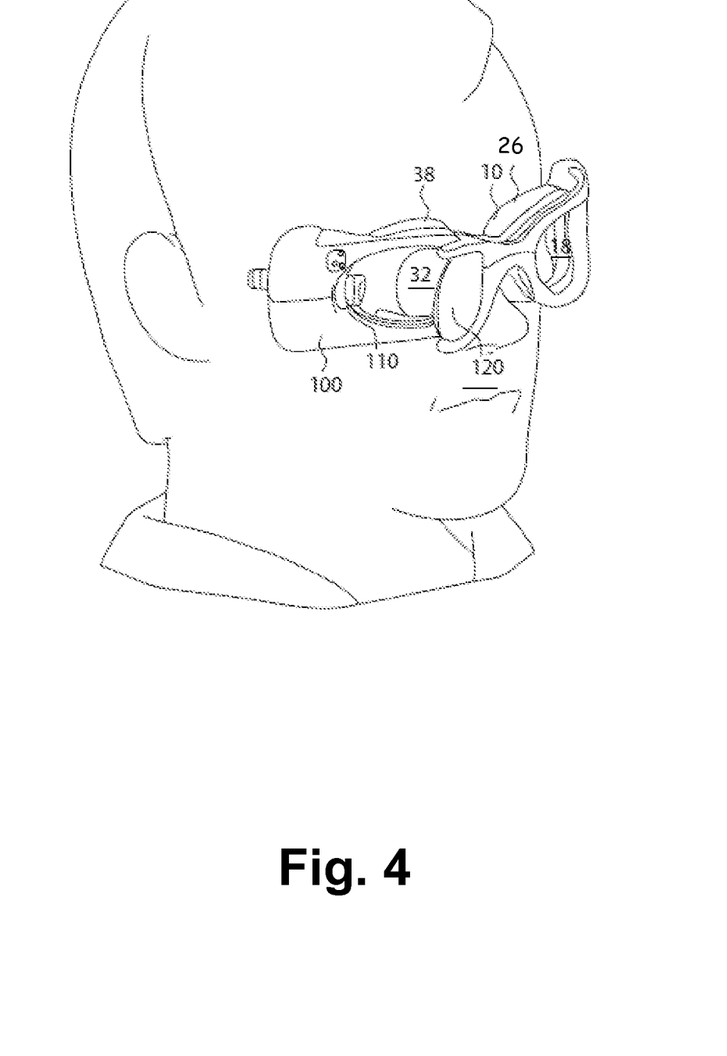

FIG. 4 shows the assembly of the new apparatus 10 shown in FIG. 1 and video goggles 100 in their intended cooperating operational positions mounted on the human's head.

The apparatus 10 with the eye piece 12 and the eye patch 14 is worn by the human underneath the separate video goggles 100. The video goggles 100 have an infrared camera 110 for observation of right eye movements, such as nystagmus. The video goggles 100 also comprise infrared light diodes (not shown) for illumination of the right eye with infrared light. The eye piece 12 has a region 32 that is transparent for infrared light and opaque to visible light. The infrared light reflected from the right eye is deflected by the mirror 120 and recorded by the infrared camera 110.

Since darkness is provided by the apparatus 10 the eye piece 12 and the eye patch 14, the separate video goggles 100 need not be opaque to visible light and in particular do not need to provide a lightproof seal around the eyes of the human, making it much easy to fit the video goggles 100 to humans with different facial anatomy. This also reduces the effort of cleaning the video goggles between uses.

FIG. 5 is a schematic exploded view of the eye piece 12 and the eye patch 14 of the apparatus 10 shown in FIG. 1.

FIG. 6 shows seen from below and with the same relative positions as in use, the eye piece 12 and the eye patch 14 of an apparatus 10 similar to the apparatus 10 shown in FIG. 1 except for the fact that the illustrated eye patch 14 also has a flap 52.

The eye patch 14 of FIG. 6 has a non-adhesive flap 52 located at the temporal end of the eye patch 14 and intended for gripping between two fingers for easy removal of the eye patch after use.

The tape 40, shown in FIG. 5, may optionally have a non-adhesive flap (not shown) residing at the temporal end of the tape 40 intended for gripping between two fingers for easy removal of the tape 40; or, the eye patch 14 together with the tape 40, after use.

Figure 7:
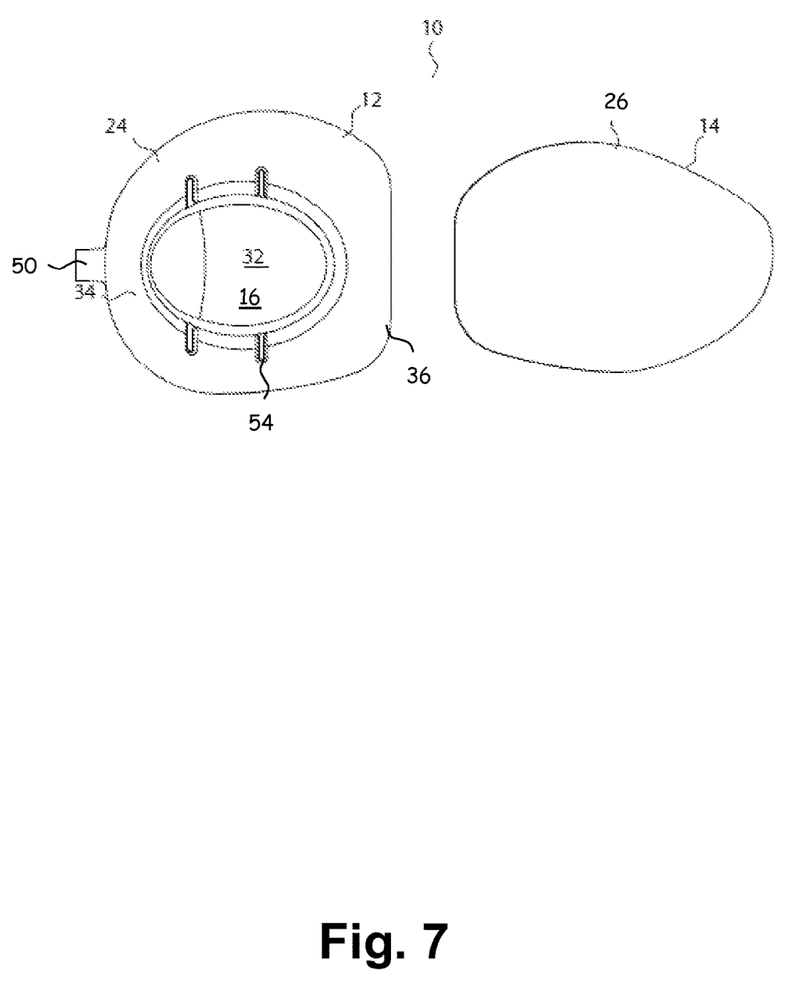
FIG. 7 is a front view of the new eye piece and new eye patch shown in FIG. 1.

FIG. 7 is a front view of the apparatus 10 shown in FIG. 1.

Figure 8:
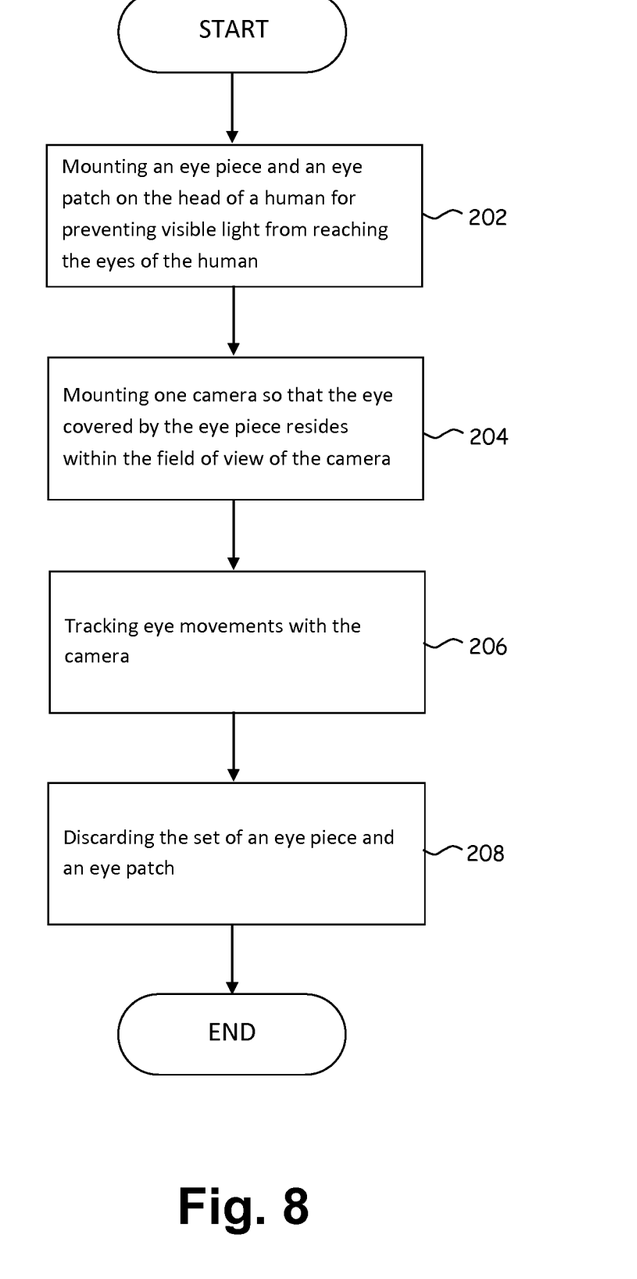
FIG. 8 is a flowchart of an example of the new method.

FIG. 8 shows a flowchart of the new method 100 comprising the steps of:

202: Mounting an apparatus with an eye piece and an eye patch, e.g. as disclosed above, on the head of a human for preventing visible light from reaching the eyes of the human, 204: Mounting one camera so that the eye of the human that is covered by the eye piece resides within the field of view of the camera, 206: Tracking eye movements with the camera, and 208: Discarding at least part of the apparatus with the eye piece and eye patch, e.g. both the eye piece and the eye patch.

When mounting the eye piece 12, the human first opens his or her eye wide so as to expand the orbicularis oculi muscles, positions the eye piece 12 over the eye, and presses the eye piece 12 against the skin surface so as to ensure a good bond between the adhesive surface 46 and the skin. Pressing the eye piece against the skin surface tends to create a small vacuum between the eye and the eye piece. This vacuum assists in retaining the eye piece 12 against the face during use. When the eye piece 12 is properly positioned, the orbicularis oculi muscles can be relaxed.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for covering eyes of a human, comprising:
an eye piece configured for covering one of the eyes of the human, the eye piece comprises an adhesive surface provided by an adhesive tape, the adhesive tape having a non-adhesive flap residing at a temporal end of the adhesive tape, the eye piece further comprising a non-adhesive flap located at a temporal end of the eye piece for easy removal of the eye piece after use; and
an eye patch configured for covering the other one of the eyes of the human, the eye patch comprising an adhesive surface provided by an adhesive tape, the adhesive tape having a non-adhesive flap residing at a temporal end of the adhesive tape, the eye patch further comprising a non-adhesive flap located at a temporal end of the eye patch for easy removal of the eye patch after use;
wherein the eye patch has a protruding section intended to cover the eye with a distance to a closed eye lid and a peripheral edge extending around the protruding section allowing the human to move the eyes without obstruction;

wherein the eye piece and the eye patch are configured for preventing transmission of visible light;

wherein the eye piece comprises a region that is transparent for electromagnetic radiation with a wavelength range outside a visible range; and wherein the eye patch is configured to also prevent transmission of invisible light.

2. The apparatus according to claim 1, wherein the eye patch has a head strap that is configured for fitting around a rear of a head of the human for securing the eye patch relative to the head of the human.

3. The apparatus according to claim 1, wherein the eye patch comprises an adhesive surface for adhesively securing the eye patch to a skin surface of the human, the adhesive surface resides on a flexible material in order to accommodates uneven facial surfaces.

4. The apparatus according to claim 3, wherein the adhesive surface comprises a layer of adhesive tape that is secured to the eye patch.

5. The apparatus according to claim 4, wherein the adhesive surface is a part of a double-sided tape, the double-sided tape having an additional adhesive surface adhering to a posterior surface of the eye patch.

6. The apparatus according to claim 1, wherein the eye piece comprises an adhesive surface for adhesively securing the eye piece to a skin surface of the human.

7. The apparatus according to claim 6, wherein the adhesive surface is on a flexible material.

8. The apparatus according to claim 6, wherein the adhesive surface comprises a layer of adhesive tape that is secured to the eye piece.

9. The apparatus according to claim 8, wherein the adhesive surface is a part of a double-sided tape, the double-sided tape having an additional adhesive surface adhering to a posterior surface of the eye piece.

10. The apparatus according to claim 1, wherein the region comprises a first material that is transparent for visible light, and a second material that is opaque to visible light, the second material coating the first material.

11. The apparatus according to claim 1, wherein the eye piece comprises a frame with an aperture for accommodation of a window that defines the region, the frame being made of a material that is different from a material of the window.

12. The apparatus according to claim 1, wherein the eye piece comprises a peripheral flange having a shape that corresponds with a shape of an orbital rim.

13. The apparatus according to claim 1, wherein the eye piece comprises (1) a transversal portion that is positioned in front of one of the eyes when the apparatus is used by the human, (2) an annular peripheral wall that surrounds the transversal portion and extends rearward therefrom, and (3) a peripheral flange surrounding the peripheral wall and having a shape that corresponds with a shape of an orbital rim of the one of the eyes.

14. A device for being worn above a shoulder of a human's body for covering eyes of the human, the device comprising:

an eyepiece that comprises an adhesive surface provided by an adhesive tape, the adhesive tape having a non-adhesive flap residing at a temporal end of the adhesive tape, the eye piece further comprising a non-adhesive flap located at a temporal end of the eye piece;

an eye patch that comprises an adhesive surface provided by an adhesive tape, the adhesive tape having a non-adhesive flap residing at a temporal end of the adhesive tape, the eye patch further comprising a non-adhesive flap located at a temporal end of the eye patch for easy removal of the eye patch after use; and at least one camera coupled to the eyepiece;

wherein the at least one camera is coupled to the eyepiece so that the region of the eye piece is positioned in a field of view of the at least one camera;

wherein the eye patch comprises a protruding section intended to cover the eye with a distance to a closed eye lid and a peripheral edge extending around the protruding section allow the human to move the eyes without obstruction, wherein the eye piece and the eye patch are configured for preventing transmission of visible light;

wherein the eye piece comprises a region that is transparent for electromagnetic radiation with a wavelength range outside a visible range; and wherein the eye patch is configured to also prevent transmission of invisible light.

15. A method of determining an eye movement, comprising:

providing an apparatus having an eye piece and an eye patch, and a camera, wherein the eye piece comprises a region that is transparent for electromagnetic radiation with a wavelength range outside a visible range;

preventing visible light from reaching eyes of a human using the eye piece and the eye patch;

preventing invisible light from reaching one of the eyes using the eye patch;

allowing the human to move the eyes without obstruction by utilizing a protruding section of the eye patch;

providing gripping to the human by a non-adhesive flap located at a temporal end of the eye piece for easy removal of the eye piece after use;

providing gripping to the human by a non-adhesive flap located at a temporal end of the eye patch for easy removal of the eye patch after use; and tracking a movement of another one of the eyes that is covered by the eye piece using the camera.

* * * * *